(12) United States Patent
Kam et al.

(10) Patent No.: US 10,842,746 B1
(45) Date of Patent: Nov. 24, 2020

(54) BI-DIRECTIONALLY CROSSLINKED LIPOSOMES AND METHOD OF MAKING SAME

(71) Applicant: Verily Life Sciences LLC, Mountain View, CA (US)

(72) Inventors: Kimberly Kam, Orinda, CA (US); Zhan Wang, San Jose, CA (US); Stephen Morton, Mountain View, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 151 days.

(21) Appl. No.: 15/685,677

(22) Filed: Aug. 24, 2017

Related U.S. Application Data

(60) Provisional application No. 62/379,447, filed on Aug. 25, 2016.

(51) Int. Cl.
*A61K 9/127* (2006.01)

(52) U.S. Cl.
CPC .................................. *A61K 9/1271* (2013.01)

(58) Field of Classification Search
CPC ......................... A61K 47/48815; A61K 31/704
See application file for complete search history.

(56) References Cited

U.S. PATENT DOCUMENTS

| | | | |
|---|---|---|---|
| 2009/0162424 A1 | 6/2009 | Cai et al. | |
| 2011/0190623 A1* | 8/2011 | Li | A61K 9/127 600/420 |
| 2012/0177724 A1* | 7/2012 | Irvine | A61K 9/1273 424/450 |
| 2015/0086484 A1* | 3/2015 | Hanes | A61K 9/1271 424/9.3 |

FOREIGN PATENT DOCUMENTS

| | | |
|---|---|---|
| WO | 0139744 | 6/2001 |
| WO | 2010091078 | 8/2010 |

OTHER PUBLICATIONS

Halter et al (Engineered Lipids That Cross-link the Inner and Outer Leaflets of Lipid Bilayers; Langmuir, 2004, 20, 2416-2423) (Year: 2004).*
Moon et al (Interbilayer-Crosslinked Multilamellar Vesicle as Synthetic Vaccine for Potent Humoral and Cellular Immune Responses; Nat Mater; Mar. 2011: 10(3): 243-251) (Year: 2011).*
Hatler et al (Engineered Lipids That Cross-Link the Inner and Outer Leaflets f Lipid Bilayers; Langmuir, 2004, 20, 2416-2423). (Year: 2004).*
Halter et al., "Engineered lipids that cross-link the inner and outer leaflets of lipid bilayers", Langmuir 20.6 (2004): 2416-2423.
Joo et al., "Crosslinked multilamellar liposomes for controlled delivery of anticancer drugs", Biomaterials 34.12 (2013): 3098-3109.
Liu et al., "Stable polymeric nanoballoons: lyophilization and rehydration of cross-linked liposomes", Journal of the American Chemical Society 124.21 (2002): 6037-6042.
Liu et al., "Codelivery of chemotherapeutics via crosslinked multilamellar liposomal vesicles to overcome multidrug resistance in tumor", PLoS One 9.10 (2014): e110611.
Liu et al., "Codelivery of doxorubicin and paclitaxel by cross-linked multilamellar liposome enables synergistic antitumor activity", Molecular pharmaceutics 11.5 (2014): 1651-1661.
Moon et al., "Interbilayer-crosslinked multilamellar vesicles as synthetic vaccines for potent humoral and cellular immune responses", Nature materials 10.3 (2011): 243-251.

\* cited by examiner

*Primary Examiner* — Micah Paul Young
(74) *Attorney, Agent, or Firm* — Kilpatrick Townsend & Stockton LLP

(57) ABSTRACT

Disclosed herein are methods for producing bi-directionally crosslinked liposomes. The methods include the steps of: providing a lipid composition comprising a plurality of reactive lipids, wherein each of the reactive lipids comprises a reactive hydrophobic group, a reactive hydrophilic group, or a reactive hydrophilic group and a reactive hydrophobic group; forming an un-crosslinked liposome comprising the reactive lipids; and crosslinking at least a portion of the reactive hydrophobic groups or the reactive hydrophilic groups; thereby producing the bi-directionally crosslinked liposomes. Bi-directionally crosslinked liposomes and methods for delivering therapeutic and/or diagnostic agents to subjects using the liposomes are also described.

20 Claims, 1 Drawing Sheet

BI-DIRECTIONALLY CROSSLINKED LIPOSOMES AND METHOD OF MAKING SAME

PRIOR RELATED APPLICATION

This application claims priority to U.S. Provisional Application No. 62/379,447, filed Aug. 25, 2016, which application is incorporated herein by reference in its entirety.

BACKGROUND OF THE INVENTION

Liposomes for drug delivery, diagnostic devices, and molecular sensing applications are attractive synthetic nanoparticle systems for a wide range of pharmaceutical applications. Liposomal drug formulations are the subject of intense investigation and have provided the first clinically-relevant nanomedicines such as DOXIL (liposomal doxorubicin). However, liposomes are limited by their stability in vivo. In the presence of serum and cells, small molecules that are incorporated into the hydrophobic leaflet have been observed to leach out and some studies suggest that lipid ejection may occur as well. Other studies suggest that specific serum proteins such as fibronectin introduce liposomal pores when they adsorb to liposome surfaces, allowing for hydrophobic small molecule leaching as well as lipid ejection/exchange. As a result, it is difficult to tune the release rate of liposomes bearing encapsulated hydrophobic loads, as well as to generate liposomal systems that are resistant to serum protein penetration and other destabilizing forces encountered in vivo. Liposome instability can also complicate manufacturing processes.

Known strategies for stabilizing liposomes include incorporation of cholesterol in lipid bilayers, radial crosslinking of multilamellar vesicles, and incorporation of lipid components with transition temperatures above physiological temperatures. Various drawbacks are associated with these strategies. Cholesterol, for example, is susceptible to oxidation and often difficult to find in pure form safe for human pharmaceutical development. Radial crosslinking of the inter-bilayers of multilamellar vesicles does not address potential radial lipid exchange/leaching. Incorporation of lipid components with higher transition temperatures are highly susceptible to protein penetration and destabilization, particularly in the absence of cholesterol and other sterols. Accordingly, new methods for production of stabilized liposomes are needed in order to provide improved nanocarriers for therapeutic agents and diagnostic agents. The present invention meets this and other needs.

BRIEF SUMMARY OF THE INVENTION

In a first embodiment, the invention provides a method of producing bi-directionally crosslinked liposomes. The method includes the steps of:
providing a lipid composition comprising a plurality of reactive lipids, wherein each of the reactive lipids comprises a reactive hydrophobic group, a reactive hydrophilic group, or a reactive hydrophilic group and a reactive hydrophobic group;
forming an un-crosslinked liposome comprising the reactive lipids; and
crosslinking at least a portion of the reactive hydrophobic groups or the reactive hydrophilic groups;
thereby producing the bi-directionally crosslinked liposomes.

In a related embodiment, the invention provides a population of bi-directionally crosslinked liposomes comprising crosslinked lipids arranged in a lipid bilayer having two leaflets, wherein the crosslinked lipids comprise a crosslinked hydrophobic group, a crosslinked hydrophilic group, or a crosslinked hydrophilic group and a crosslinked hydrophobic group, and wherein the bi-directionally crosslinked liposomes are radially crosslinked and circumferentially crosslinked.

In another embodiment, the invention provides a method of delivering a diagnostic agent or therapeutic agent to a subject in need thereof. The method includes administering a population of bi-directionally crosslinked liposomes as described herein to a subject in need thereof, wherein the liposomes contain a therapeutic agent, a diagnostic agent, or a combination thereof.

DETAILED DESCRIPTION OF THE INVENTION

Figure 1A:
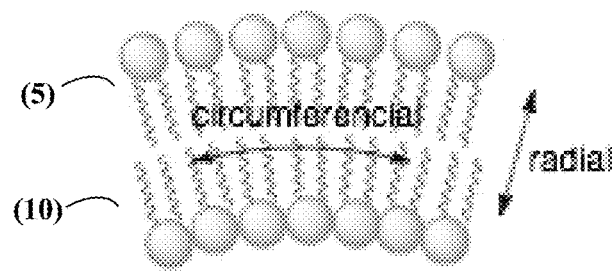
FIG. 1A shows the radial and circumferential dimensions of a lipid bilayer.

The methods disclosed herein provide a number of advantages for preparing useful liposomes. The methods allows for high tunability of physical properties (e.g., membrane elastic modulus) which, in turn, enhance liposome pharmacokinetic properties. The versatile crosslinking process also allows for control of therapeutic cargo release from the liposomes. Bi-directional crosslinking can prevent the exchange of liposome components between leaflets in lipid bilayers and can also prevent unwanted leaching/ejection of cargo from the liposomes. Furthermore, bi-directionally crosslinked liposomes can be used under a broader range of conditions, such as the harsh environment of the gastrointestinal tract. Acid, bile salts, and phospholipases in this environment will degrade conventional liposome components such as cholesterol, limiting the utility of the liposomes for oral drug delivery. The methods disclosed herein also allow for the incorporation of bioactive targeting groups and the preparation of stable, sub-100 nm liposomes. These smaller nanoparticles are difficult to fabricate with known techniques due to the unstable, high membrane curvature that is required for smaller particles.

I. Definitions

As used herein, the term "lipid" refers to molecules including fats, waxes, steroids, cholesterol, fat-soluble vitamins, monoglycerides, diglycerides, phospholipids, sphingolipids, glycolipids, cationic or anionic lipids, derivatized lipids, and the like, as described in detail below. Lipids are typically amphiphilic compounds containing hydrophilic regions and hydrophobic regions. Lipids may self-assemble to form micelles and membranes (i.e., thin sheets of lipid molecules) including monolayer membranes and bilayer membranes. The lipids may assemble in solution to form liposomes. A "reactive" lipid (or a "reactive group" with a lipid) is a lipid capable of forming covalent bonds with lipids or other liposome components.

As used herein, the term "hydrophobic group" refers to a non-polar moiety that resists dissolution in water. Examples of hydrophobic groups include, but are not limited to, long-chain acyl groups (e.g., palmitoyl groups or stearoyl groups) present in phospholipids, sphingolipids, and the like. As used herein, the term "hydrophilic group" refers to a polar moiety that is water-soluble. Examples of hydrophilic groups include, but are not limited to, ethanolamine and glycerol headgroups in phospholipids as well as carboxylate groups in steroid acids such as cholate.

As used herein, the term "liposome" encompasses any compartment enclosed by a lipid membrane. The term liposome includes unilamellar vesicles which are comprised of a single lipid bilayer (e.g., a phospholipid bilayer) and generally have a diameter in the range of about 20 to about 400 nm. Liposomes can also be multilamellar, which generally have a diameter in the range of 1 to 10 am. In some embodiments, liposomes can include multilamellar vesicles (MLVs; from about 1 µm to about 10 µm in size), large unilamellar vesicles (LUVs; from a few hundred nanometers to about 10 µm in size), and small unilamellar vesicles (SUVs; from about 20 nm to about 200 nm in size). Average liposome size can be determined by a number of techniques including dynamic light scattering (DLS), quasi-elastic light scattering (QELS), and electron microscopy. DLS and QELS determine a hydrodynamic diameter—that is, the average diameter of the particle as it tumbles and rotates in solution.

As used herein, the term "polydispersity index" refers to the size distribution of a population of liposomes. Polydispersity index can be determined by a number of techniques including dynamic light scattering (DLS), quasi-elastic light scattering (QELS), and electron microscopy. Polydispersity index (PDI) is usually calculated as:

$$PdI = \left(\frac{\sigma}{d}\right)^2,$$

i.e., the square of (standard deviation/mean diameter).

As used herein, the term "crosslinker" refers to a reagent having chemical moieties capable of forming covalent bonds between component lipids (and/or between lipids and other components) in a liposome. Crosslinkers may crosslink the component lipids by any number of reaction mechanisms, such as nucleophilic substitution reactions, radical reactions, cycloaddition reactions, and/or "click" reactions as described below. A "non-lipid" crosslinking reagent refers to a reagent that is not any of the lipids described above. Examples of non-lipid crosslinking reagents include, but are not limited to, non-lipid N-hydroxysuccinimidyl (NHS) esters and N-hydroxysulfosuccinimidyl (sulfo-NHS) esters, non-lipid maleimides, non-lipid aryl azides and non-lipid fluorinated aryl azides, and pentafluorophenyl (PFP) esters, as described in more detail below. The term "crosslinking" refers to the formation of covalent bonds between lipids (and/or between lipids and other components) in a liposome.

As used herein, the term "radial" crosslinking refers to the formation of covalent bonds between lipids in two different lamellae of a multilamellar liposome, or between lipids in two layers of a lipid bilayer in a unilamellar liposome. "Circumferential" crosslinking refers to the formation of covalent bonds between lipids in the same lamella of a multilamellar liposome, or between lipids in the same layer of a lipid bilayer in a unilamellar liposome. "Bi-directional" crosslinking refers to crosslinking in both the radial and circumferential directions.

As used herein, the terms "alkyne" and "alkynyl" refer to either a straight chain or branched hydrocarbon having at least 2 carbon atoms and at least one triple bond. Alkynyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. A "terminal" alkyne refers to an alkyne wherein the triple bond is between two carbon atoms at the end of the hydrocarbon chain (e.g., hex-1-yne). An "internal" alkyne refers to an alkyne wherein the triple bond is between two carbon atoms that are not at the end of the hydrocarbon chain (e.g., hex-3-yne).

As used herein, the term "azide" refers to a functional group having the structure $-N_3$.

As used herein, the term "phosphine" refers to a functional group having the formula $-PR_3$, wherein each R group is independently selected from the group consisting of alkyl, cycloalkyl, and aryl, each of which is optionally substituted as described below.

As used herein, the term "alkyl," by itself or as part of another substituent, refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted. "Substituted alkyl" groups can be substituted with one or more groups selected from halo, hydroxy, amino, alkylamino, amido, acyl, nitro, cyano, and alkoxy.

As used herein, the term "alkoxy," by itself or as part of another substituent, refers to a group having the formula $-OR$, wherein R is alkyl.

As used herein, the term "cycloalkyl," by itself or as part of another substituent, refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to cyclopropyl, cyclobutyl, cyclopentyl, and cyclohexyl. Cycloalkyl groups can be substituted or unsubstituted. "Substituted cycloalkyl" groups can be substituted with one or more groups selected from halo, hydroxy, amino, alkylamino, amido, acyl, nitro, cyano, and alkoxy. The term "lower cycloalkyl" refers to a cycloalkyl radical having from three to seven carbons including, for example, cyclopropyl, cyclobutyl, cyclopentyl, cyclohexyl, and cycloheptyl.

As used herein, the terms "halo" and "halogen," by themselves or as part of another substituent, refer to a fluorine, chlorine, bromine, or iodine atom or radical.

As used herein, the term "aryl," by itself or as part of another substituent, refers to an aromatic ring system having any suitable number of ring atoms and any suitable number of rings. Aryl groups can include any suitable number of ring atoms, such as 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic (e.g., benzocyclohexyl) or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted. "Substituted aryl" groups can be substituted with one or more groups selected from halo, hydroxy, amino, alkylamino, amido, acyl, nitro, cyano, and alkoxy.

As used herein, the term "amino" refers to a moiety —$NR_3$, wherein each R group is H or alkyl. An amino moiety can be ionized to form the corresponding ammonium cation.

As used herein, the term "hydroxy" refers to the moiety —OH.

As used herein, the term "thiol" refers to the moiety —SH.

As used herein, the term "cyano" refers to a carbon atom triple-bonded to a nitrogen atom (i.e., the moiety —C≡N).

As used herein, the term "carboxy" refers to the moiety —C(O)OH. A carboxy moiety can be ionized to form the corresponding carboxylate anion.

As used herein, the term "amido" refers to a moiety —NRC(O)R or —C(O)$NR_2$, wherein each R group is H or alkyl.

As used herein, the term "nitro" refers to the moiety —$NO_2$.

As used herein, the term "composition" refers to a product (e.g., a mixture of lipids used for forming a liposome) comprising the specified ingredients in the specified amounts, as well as any product which results, directly or indirectly, from combination of the specified ingredients in the specified amounts.

As used herein, the terms "delivery" and "delivering" refer to conveyance of a therapeutic agent to a subject using the methods of the invention. Delivery may be localized to a particular location in a subject, such as a tissue, an organ, or cells of a particular type.

As used herein, the term "therapeutic agent" refers to a compound or molecule that, when present in an effective amount, produces a desired therapeutic effect on a subject in need thereof. The present invention contemplates a broad range of therapeutic agents and their use in conjunction with the liposome compositions, as further described herein.

As used herein, the term "diagnostic agent" refers to a component that can be directly or indirectly detected in a test sample (e.g., a blood, plasma, or tissue sample) or a subject (e.g., using an in vivo imaging technique). In some embodiments, the diagnostic agent can be used to detect, image, and/or monitor the presence and/or progression of a condition, pathological disorder, or disease in the subject.

As used herein, the term "subject" refers to any mammal, in particular a human, at any stage of life.

"About" and "around," as used herein to modify a numerical value, indicate a defined range around that value. If "X" were the value, "about X" or "around X" would generally indicate a value from 0.95X to 1.05X including, for example, from 0.98X to 1.02X or from 0.99X to 1.01X. Any reference to "about X" or "around X" specifically indicates at least the values X, 0.95X, 0.96X, 0.97X, 0.98X, 0.99X, 1.01X, 1.02X, 1.03X, 1.04X, and 1.05X. Thus, "about X" and "around X" are intended to teach and provide written description support for a claim limitation of, e.g., "0.98X."

II. Methods of Producing Bi-Directionally Crosslinked Liposomes

In a first aspect, the invention provides a method of producing bi-directionally crosslinked liposomes, comprising the steps of: providing a lipid composition comprising a plurality of reactive lipids, wherein each of the reactive lipids comprises a reactive hydrophobic group, a reactive hydrophilic group, or a reactive hydrophilic group and a reactive hydrophobic group; forming an un-crosslinked liposome comprising the reactive lipids; and crosslinking at least a portion of the reactive hydrophobic groups or the reactive hydrophilic groups; thereby producing the bi-directionally crosslinked liposomes. In some embodiments, the method includes crosslinking the reactive hydrophobic groups without crosslinking the reactive hydrophilic groups. In some embodiments, the method includes crosslinking the reactive hydrophobic groups and crosslinking the reactive hydrophilic groups. In some embodiments, the method includes crosslinking the reactive hydrophilic groups of multilamellar liposomes.

A schematic representation of a lipid bilayer is shown in FIG. 1A. A liposome's "radial" direction extends across two layers (5) and (10) of a lipid bilayer in a unilamellar liposome, as shown in FIG. 1A. Alternatively, the radial direction extends across two different lamellae of a multilamellar liposome. A liposome's "circumferential" direction extends around the same layer of a lipid bilayer in a unilamellar liposome (i.e., around the liposome's circumference or a portion thereof) as shown in FIG. 1A. Alternatively, the circumferential directions extends around the same lamella of a multilamellar liposome.

Figure 1B:
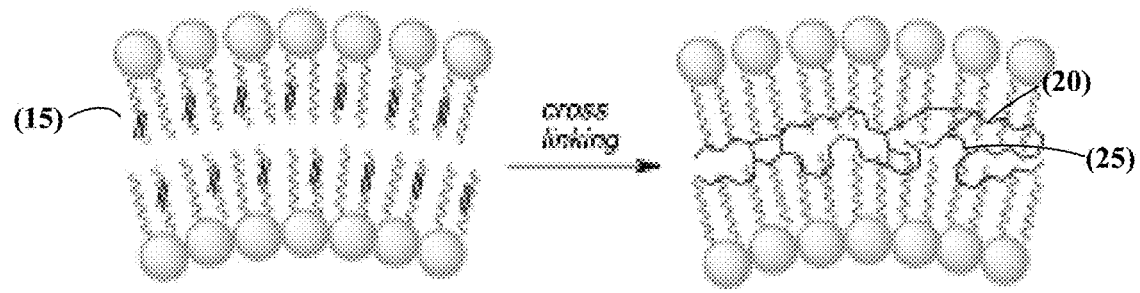
FIG. 1B shows bi-directional crosslinking of a lipid bilayer via crosslinking of lipid hydrophobic groups.
Figure 1C:
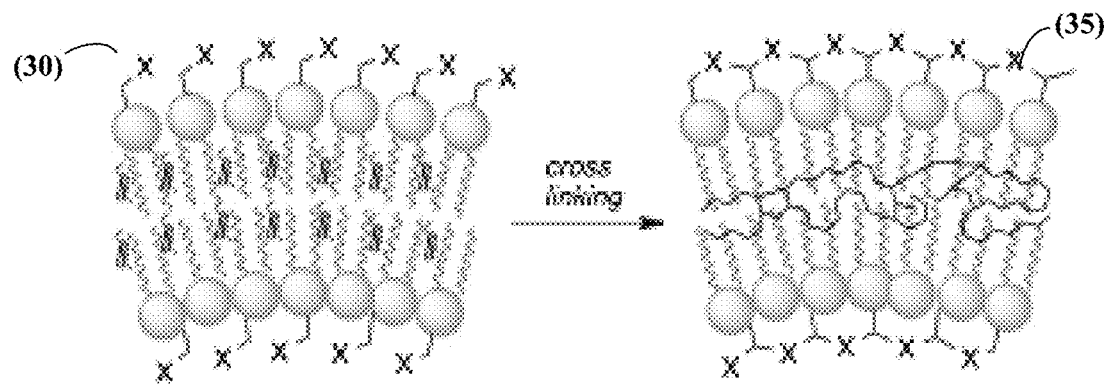
FIG. 1C shows bi-directional crosslinking of a lipid bilayer via crosslinking of lipid hydrophobic groups and lipid hydrophilic groups.

As shown in FIG. 1B, crosslinking in both the radial direction and the circumferential direction can be accomplished by crosslinking a portion of the reactive hydrophobic groups (15). In this way, covalent bonds (20) may be formed between lipids in two different layers of a lipid bilayer. Covalent bonds (25) may also be formed between lipids in different layers of the lipid bilayer. As shown in FIG. 1C, covalent bonds (35) may also be formed between lipids in the same layer of a lipid bilayer by crosslinking a portion of the reactive hydrophilic groups (30). Accordingly, some embodiments of the invention provide methods wherein the reactive lipids in the un-crosslinked liposome are arranged in a lipid bilayer having two leaflets. In some embodiments, crosslinking the reactive hydrophobic groups comprises forming covalent bonds between the reactive hydrophobic groups of adjacent reactive lipids within the same leaflet. In some embodiments, crosslinking the reactive hydrophobic groups comprises forming covalent bonds between the reactive hydrophobic groups of adjacent reactive lipids across leaflets.

The methods of the invention can be used to prepare liposomes containing a variety of lipids, including fats, waxes, steroids, sterols, cholesterol, fat-soluble vitamins, monoglycerides, diglycerides, phospholipids, sphingolipids, glycolipids, cationic or anionic lipids, derivatized lipids, and the like. The lipid composition used in the methods of the invention may contain any number of reactive lipids and non-lipid crosslinkers. Any suitable reactive lipid, non-lipid crosslinker, or combination thereof can be used for preparing the liposomes. Suitable reactive lipids and non-lipid crosslinkers generally include reactive groups capable of forming covalent bonds between two or more component lipids in a liposome. In some cases, the liposomes may be prepared by forming covalent bonds between reactive lipids without the use of a non-lipid crosslinker. Alternatively, a non-lipid crosslinker can be used to form covalent bonds between two or more lipids. The formation of covalent bonds between component lipids can be promoted by subjecting lipid/crosslinker mixtures to elevated temperatures, radiation, reducing conditions, or oxidizing conditions. In some embodiments, the crosslinking step comprises subjecting the un-crosslinked liposomes to heat. In some embodiments, the crosslinking step comprises subjecting the un-crosslinked liposomes to UV radiation.

In some embodiments, reactive lipids are crosslinked via one or more click reactions. As used herein, "click reaction" refers to a chemical reaction characterized by a large thermodynamic driving force that usually results in irreversible covalent bond formation. Click reactions can often be conducted in aqueous or physiological conditions without producing cytotoxic byproducts. Examples of click reactions include [3+2] cycloadditions, such as the Huisgen 1,3-dipolar cycloaddition reaction of an azide and an alkyne; thiol-ene reactions, such as the Michael addition of a thiol to a maleimide or other unsaturated acceptor; [4+1] cycloaddition reactions between an isonitrile and a tetrazine; the Staudinger ligation between an azide and an ester-functionalized phosphine or an alkanethiol-functionalized phosphine; Diels-Alder reactions (e.g., between a furan and a maleimide); and inverse electron demand Diels-Alder reactions (e.g., between a tetrazine and a dienophile such as a strained transcyclooctene). As used herein, a "clickable moiety" refers to a functional group that is capable of forming a covalent bond via a click reaction, such as an azide, an alkyne, a phosphine, a thiol, a maleimide, an isonitrile, or a tetrazine. Accordingly, some embodiments of the invention provide methods wherein the crosslinkers include clickable moieties. In some embodiments, each clickable moiety is independently selected from the group consisting of an azide, an alkyne, and a phosphine.

As noted above, the reactive lipids may have a reactive hydrophilic group (i.e., a reactive headgroup), a reactive hydrophobic group (i.e., a reactive tailgroup), or both. In some embodiments, the reactive lipid is an alkyne-functionalized reactive lipid. Examples of alkyne-functionalized reactive lipids include, but are not limited to, 27-norcholest-5-en-25-yn-3β-ol (also referred to as alkyne-cholesterol, corresponding to CAS No. 1631985-09-5); 27-alkyne cholesterol (corresponding to CAS No. 1527467-07-7); 5Z,8Z,11Z,14Z-eicosatetraen-19-ynoic acid (also referred to as arachidonic acid-alkyne, corresponding to CAS No. 1219038-32-0); 1,2-distearoyl-sn-glycero-3-phosphoetha- nolamine-N-[dibenzocyclooctyl(polyethylene glycol)-2000] (also referred to as DSPE-PEG(2000)-DBCO) and salts thereof; 1,2-dipalmitoyl-sn-glycero-3-phosphoethanolamine-N-(5-hexynoyl) (also referred to as hexynoyl PE) and salts thereof; 1,2-dipalmitoyl-sn-glycero-3-phosphoethanolamine-N-dibenzocyclooctyl (also referred to as 16:0 DBCO PE); 1,2-dioleoyl-sn-glycero-3-phosphoethanolamine-N-dibenzocyclooctyl (also referred to as 18:1 DBCO PE); 15-hexadecynoic acid (also referred to as palmitic acid (15-yne)); (Z)-octadec-9-en-17-ynoic acid (also referred to as oleic acid(17-yne)); 1,2-bis(10,12-tricosadiynoyl)-sn-glycero-3-phosphocholine (also referred to as 23:2 Diyne PC and DC(8,9)PC, corresponding to CAS No. 76078-28-9); 1-palmitoyl-2-(10,12-tricosadiynoyl)-sn-glycero-3-phosphocholine (also referred to as 16:0-23:2 diyne PC and PTPC, corresponding to CAS. No. 84271-00-1); 1,2-bis(10,12-tricosadiynoyl)-sn-glycero-3-phosphoethanolamine (also referred to as 23:2 Diyne PE and DC(8,9)PE, corresponding to CAS No. 144750-73-2); and 1-palmitoyl-2-(10,12-tricosadiynoyl)-sn-glycero-3-phosphoethanolamine (also referred to as 16:0-23:2 diyne PE and PTPE). Alkyne-functionalized reactive lipids can participate in click reactions such as the Huisgen 1,3-dipolar cycloaddition as described above or photo-crosslinking reactions as described below.

Accordingly, some embodiments of the invention provide methods wherein each reactive lipid is independently selected from the group consisting of 1,2-bis(10,12-tricosadiynoyl)-sn-glycero-3-phosphocholine; 1-palmitoyl-2-(10,12-tricosadiynoyl)-sn-glyc-ero-3-phosphocholine; 1,2-bis(10,12-tricosadiynoyl)-sn-glycero-3-phosphoethanolamine; and 1-palmitoyl-2-(10,12-tricosadiynoyl)-sn-glycero-3-phosphoethanolamine.

In some embodiments, the reactive lipid is an azide-functionalized reactive lipid. Examples of azide-functionalized reactive lipids include, but are not limited to, (1,2-distearoyl-sn-glycero-3-phosphoethanolamine-N-[azido (polyethylene glycol)-2000] (also referred to as DSPE-PEG (2000) azide) and salts thereof, as well as 1,2-dipalmitoyl-sn-glycero-3-phosphoethanolamine-N-(6-azidohexanoyl) (also referred to as 16:0 azidocaproyl PE) and salts thereof. Azide-functionalized reactive lipids can participate in click reactions such as the Huisgen 1,3-dipolar cycloaddition reaction and the Staudinger ligation as described above. Nitrene groups, generated by expulsion of nitrogen gas upon exposure of azide-functionalized reactive lipids to light or elevated temperatures, can also form covalent bonds via insertion into C—H bonds of adjacent lipids.

Other reactive lipids may also be used in the methods of the invention. Further examples of reactive lipids include, but are not limited to, hex-5'-ynyl 3β-hydroxy-6-diazirinyl-5α-cholan-24-oate (corresponding to CAS No. 1485490-47-8); N-(9-(3-pent-4-ynyl-3-H-diazirin-3-yl)-nonanoyl)-D-erythro-sphingosine (corresponding to CAS No. 1262788-58-8); D-galactosyl-β-1,1' N-(9-(3-pent-4-ynyl-3-H-diazirin-3-yl)-nonanoyl)-D-erythro-sphingosine; D-glucosyl-β-1,1' N-(9-(3-pent-4-ynyl-3-H-diazirin-3-yl)-nonanoyl)-D-erythro-sphingosine; 1-palmitoyl-2-(9-(3-pent-4-ynyl-3-H-diazirin-3-yl)-nonanoyl)-sn-glycero-3-phosphocholine; and 1-(9-(3-pent-4-ynyl-3-H-diazirin-3-yl)-nonanoyl)-2-oleoyl-sn-glycero-3-phosphocholine.

Reactive lipids may further include phospholipids with reactive hydrophilic groups (i.e., reactive headgroups). Example of such reactive phospholipids include, but are not limited to, phosphatidylethanolamines (PEs) and phosphatidylglycerols (PGs). Examples of such phospholipids include, but are not limited to, dimyristoylphosphatidylglycerol (DMPG), distearoylphosphatidylglycerol (DSPG), dioleoylphosphatidylglycerol (DOPG), dipalmitoyl-phosphatidylglycerol (DPPG), dimyristoylphosphatidylserine (DMPS), distearoyl-phosphatidylserine (DSPS), dioleoylphosphatidylserine (DOPS), dipalmitoylphosphatidylserine (DPPS), dioleoylphosphatidylethanolamine (DOPE), palmitoyloleoylphosphatidylethanolamine (POPE), dipalmitoylphosphatidylethanolamine (DPPE), dimyristoylphosphoethanolamine (DMPE), distearoylphosphatidylethanolamine (DSPE), 16-O-monomethyl PE, 16-O-dimethyl PE, 18-1-trans PE, 1-stearoyl-2-oleoyl-phosphatidyethanolamine (SOPE), and dielaidoylphos-phoethanolamine (transDOPE). Reactive phospholipid headgroups may be chemically modified with a clickable moiety for further reaction; for example, an ethanolamine head group can be modified with an alkyne-containing carboxylic acid (e.g., hex-5-ynoic acid) using a suitable coupling reagent (e.g., 1-ethyl-3-(3-dimethylaminopropyl)carbodiimide) for further reaction via a Huisgen 1,3-dipolar cycloaddition. Reactive headgroups of adjacent phospholipids may also be covalently bonded to one another using the homobifunctional crosslinkers or heterobifunctional crosslinkers described below.

Phospholipids may further include reactive functional groups for further derivatization. Examples of such reactive lipids include, but are not limited to, dioleoylphosphatidylethanolamine-4-(N-maleimidomethyl)-cyclohexane-1-carboxylate (DOPE-mal) and dipalmitoylphosphatidylethanolamine-N-succinyl (succinyl-PE).

In some embodiments, the lipid composition further comprises non-reactive lipids. In some embodiments, each of the non-reactive lipids is independently selected from the group consisting of a phosphatidylcholine, a PEGylated phosphatidylethanolamine, and a sterol.

Suitable phosphatidylcholine lipids include saturated PCs and unsaturated PCs. Examples of saturated PCs include 1,2-dilauroyl-sn-glycero-3-phosphocholine (DLPC), 1,2-dimyri stoyl-sn-glycero-3-phosphocholine (dimyristoyl-phosphatidylcholine; DMPC), 1,2-distearoyl-sn-glycero-3-phosphocholine (distearoylphosphatidylcholine; DSPC), 1,2-dioleoyl-sn-glycero-3-phosphocholine (DOPC), 1,2-dipalmitoyl-sn-glycero-3-phosphocholine (dipalmitoyl-phosphatidylcholine; DPPC), 1-myristoyl-2-palmitoyl-sn-glycero-3-phosphocholine (MPPC), 1-palmitoyl-2-myristoyl-sn-glycero-3-phosphocholine (PMPC), 1-myristoyl-2-stearoyl-sn-glycero-3-phosphocholine (MSPC), 1-palmitoyl-2-stearoyl-sn-glycero-3-phosphocholine (PSPC), 1-stearoyl-2-palmitoyl-sn-glycero-3-phosphocholine (SPPC), and 1-stearoyl-2-myristoyl-sn-glycero-3-phosphocholine (SMPC).

Examples of unsaturated PCs include, but are not limited to, 1,2-dimyristoleoyl-sn-glycero-3-phosphocholine, 1,2-dimyristelaidoyl-sn-glycero-3-phosphocholine, 1,2-dipalmito-leoyl-sn-glycero-3-phosphocholine, 1,2-dipalmitelaidoyl-sn-glycero-3-phosphocholine, 1,2-dioleoyl-sn-glycero-3-phosphocholine (DOPC), 1,2-dielaidoyl-sn-glycero-3-phosphocholine, 1,2-dipetroselenoyl-sn-glycero-3-phosphocholine, 1,2-dilinoleoyl-sn-glycero-3-phosphocholine, 1-palmitoyl-2-oleoyl-sn-glycero-3-phosphocholine (palmitoyloleoylphosphatidylcholine; POPC), 1-palmitoyl-2-linoleoyl-sn-glycero-3-phosphocholine, 1-stearoyl-2-oleoyl-sn-glycero-3-phosphocholine (SOPC), 1-stearoyl-2-linoleoyl-sn-glycero-3-phosphocholine, 1-oleoyl-2-myrist-oyl-sn-glycero-3-phosphocholine (OMPC), 1-oleoyl-2-palmitoyl-sn-glycero-3-phosphocholine (OPPC), and 1-oleoyl-2-stearoyl-sn-glycero-3-phosphocholine (OSPC). Lipid extracts, such as egg PC, heart extract, brain extract, liver extract, soy PC, and hydrogenated soy PC (HSPC) are also useful in the present invention. Other phospholipids including, but are not limited to, phosphatidic acids (PAs), phosphatidylserines (PSs), and phosphatidylinositols (PIs) may also be used in the lipid compositions.

In some embodiments, the lipid composition further contains one or more steroids, characterized by the presence of a fused, tetracyclic gonane ring system. Examples of steroids include, but are not limited to, cholic acid, progesterone, cortisone, aldosterone, testosterone, dehydroepiandrosterone, and sterols such as estradiol and cholesterol. Synthetic steroids and derivatives thereof are also contemplated for use in the present invention. In some embodiments, however, the lipid compositions and liposomes are substantially free of cholesterol or cholesterol derivatives.

In some embodiments, the lipid composition further contains a (polyethylene glycol)-lipid (i.e., a "PEG-lipid"). The presence of PEG on the surface of a liposome has been shown to extend blood-circulation time while reducing mononuclear phagocyte system uptake, creating so-called "stealth" liposomes as described in U.S. Pat. Nos. 5,013,556 and 5,827,533, each of which is hereby incorporated by reference in its entirety.

The lipid composition may include any suitable PEG-lipid. In some embodiments, the PEG-lipid is a PEGylated phosphatidylethanolamine (e.g., a diacyl-phosphatidylethanolamine-N-[methoxy(polyethylene glycol)]). The molecular weight of the poly(ethylene glycol) in the PEG-lipid is generally in the range of from about 500 Daltons (Da) to about 5000 Da. The poly(ethylene glycol) can have a molecular weight of, for example, about 750 Da, about 1000 Da, about 2500 Da, or about 5000 Da, or about 10,000 Da, or any molecular weight within this range. In some embodiments, the PEG-lipid is selected from distearoyl-phosphatidylethanolamine-N-[methoxy(polyethylene glycol)-2500] (DSPE-PEG-2500) and distearoyl-phosphatidyl ethanolamine-N-[methoxy(polyethylene glycol)-5000] (DSPE-PEG-5000). In some embodiments, the PEG-lipid is DSPE-PEG-2500. In some embodiments, the PEG-lipid is DSPE-PEG-5000.

In some embodiments, the lipid composition comprises crosslinkers which are not lipids themselves but which contain reactive groups that form covalent bonds between component lipids. A wide variety of non-lipid crosslinking reagents with such reactive groups are known in the art. The crosslinking reagents can react to form covalent bonds with functional groups in the component lipids (e.g., a primary amine headgroup in a phosphatidylethanolamine; a thiol headgroup in a phosphatidylthioethanol; a carboxylate headgroup in a phosphatidic acid; a hydroxyl group in a phosphatidylglycerol; and the like). Examples of crosslinking reagents include, but are not limited to, N-hydroxysuccinimidyl (NHS) esters and N-hydroxysulfosuccinimidyl (sulfo-NHS) esters (amine reactive); carbodiimides (amine and carboxyl reactive); hydroxymethyl phosphines (amine reactive); maleimides (thiol reactive); halogenated acetamides such as N-iodoacetamides (thiol reactive); aryl azides (primary amine reactive); fluorinated aryl azides (reactive via carbon-hydrogen (C—H) insertion); pentafluorophenyl (PFP) esters (amine reactive); imidoesters (amine reactive); isocyanates (hydroxyl reactive); vinyl sulfones (thiol, amine, and hydroxyl reactive); pyridyl disulfides (thiol reactive); and benzophenone derivatives (reactive via C—H bond insertion). Further reagents include but are not limited to those described in Hermanson, *Bioconjugate Techniques* 2nd Edition, Academic Press, 2008.

Crosslinkers useful in the methods of the invention include homobifunctional crosslinkers, which react with the same functional group in two component lipid molecules (e.g., a primary amine headgroup in each of two phosphatidylethanolamine molecules), as well as heterobifunctional crosslinkers, which react with different functional groups in two component lipid molecules (e.g., a primary amine headgroup in a phosphatidylethanolamine molecule and a thiol headgroup in a phosphatidylthioethanol).

Examples of homobifunctional crosslinkers include, but are not limited to, amine-reactive homobifunctional crosslinkers (e.g., dimethyl adipimidate, dimethyl suberimidate, dimethyl pimilimidate, disuccinimidyl glutarate, disuccinimidyl suberate, bis(sulfosuccinimidyl) suberate, bis(diazobenzi dine), ethylene glycobis(succinimidylsuccinate), disuccinimidyl tartrate, disulfosuccinimidyl tartrate, glutaraldehyde, dithiobis(succinimidyl pro-pionate), dithiobis-(sulfosuccinimidyl propionate), dimethyl 3,3'-dithiobispropionimidate, bis 2-(succinimidyl-oxycarbonyloxy)ethylsulfone, and the like) as well as thiol-reactive homobifunctional crosslinkers (e.g., bismaleidohexane, 1,4-bis-[3-(2-pyridyldithio)propionamido]butane, and the like). Examples of heterobifunctional crosslinkers include, but are not limited to, amine- and thiol-reactive crosslinkers (e.g., succinimidyl 4-(N-maleimidomethyl)-cyclohexane-1-carboxylate, m-maleimidobenzoyl-N-hydroxysuccinimide ester, succinimidyl-4-(p-maleimidophenyl)butyrate, N-(y-maleimidobutyryloxy)succinimide ester, N-succinimidyl(4-iodoacetyl) aminobenzoate, 4-succinimidyl oxycarbonyl-α-(2-pyridyldithio)-toluene, sulfosuccinimidyl-6-α-methyl-α-(2-pyridyldithio)-toluamido-hexanoate, N-succinimidyl-3-(2-pyridyldithio) propionate, N-hydroxysuccinimidyl 2,3-dibromopropionate, and the like).

Crosslinking reactions are conducted under conditions for forming covalent bonds between component lipids in the liposomes. The reactions may be conducted at any suitable temperature. In general, the reactions are conducted at a temperature of from about 4° C. to about 50° C. The reactions can be conducted, for example, at about 25° C. or about 37° C. The reactions can be conducted at any suitable pH. In general, the reactions are conducted at a pH of from about 4.5 to about 10. The reactions can be conducted, for example, at a pH of from about 5 to about 9. In some embodiments, the reaction is conducted at a pH ranging from 7.2 to 7.5. The reactions can be conducted for any suitable length of time. In general, the reaction mixtures are incubated under suitable conditions for anywhere between about 1 minute and several hours. The reactions can be conducted, for example, for about 1 minute, or about 5 minutes, or about 10 minutes, or about 30 minutes, or about 1 hour, or about 2 hours, or about 4 hours, or about 8 hours, or about 12 hours, or about 24 hours. Other reaction conditions may be used in the methods of the invention, depending on the particular lipids and/or crosslinkers employed. In some embodiments, crosslinking within the same leaflet of a lipid bilayer (i.e., circumferential crosslinking) is conducted before crosslinking across different leaflets (i.e., radial crosslinking). In some embodiments, crosslinking across different leaflets in a lipid bilayer (i.e., radial crosslinking) is conducted place before crosslinking within the same leaflet (i.e., circumferential crosslinking).

Reaction mixtures containing the liposomes may contain other reagents of the sort typically used in crosslinking reactions. For example, in certain embodiments, the reaction mixtures can contain buffers (e.g., 2-(N-morpholino)ethanesulfonic acid (MES), 2-[4-(2-hydroxyethyl)piperazin-1-yl]ethanesulfonic acid (HEPES), 3-morpholinopropane-1-sulfonic acid (MOPS), 2-amino-2-hydroxymethyl-propane-1,3-diol (TRIS), potassium phosphate, sodium phosphate, phosphate-buffered saline, sodium citrate, sodium acetate, and sodium borate), cosolvents (e.g., dimethylsulfoxide, dimethylformamide, ethanol, methanol, tetrahydrofuran, acetone, and acetic acid), salts (e.g., NaCl, KCl, $CaCl_2$, and salts of $Mn^{2+}$ and $Mg^{2+}$), detergents/surfactants (e.g., a non-ionic surfactant such as N,N-bis[3-(D-gluconamido) propyl]cholamide, polyoxyethylene (20) cetyl ether, dimethyldecylphosphine oxide, branched octylphenoxy poly (ethyleneoxy)ethanol, a polyoxyethylene-polyoxypropylene block copolymer, t-octylphenoxypolyethoxyethanol, polyoxyethylene (20) sorbitan monooleate, and the like; an anionic surfactant such as sodium cholate, N-lauroylsarcosine, sodium dodecyl sulfate, and the like; a cationic surfactant such as hexdecyltrimethyl ammonium bromide, trimethyl(tetradecyl) ammonium bromide, and the like; or a zwitterionic surfactant such as an amidosulfobetaine, 3-[(3-cholamidopropyl)dimethyl-ammonio]-1-propanesulfonate, and the like), chelators (e.g., ethylene glycol-bis(2-aminoethylether)-N,N,N',N'-tetraacetic acid (EGTA), 2-({2-[bis(carboxymethyl)amino]ethyl} (carboxymethyl)amino)acetic acid (EDTA), and 1,2-bis(o-aminophenoxy)ethane-N,N,N', N'-tetraacetic acid (BAPTA)), and reducing agents (e.g., dithiothreitol (DTT), (3-mercaptoethanol (BME), and tris(2-carboxyethyl)phosphine (TCEP)). Buffers, cosolvents, salts, detergents/surfactants, chelators, and reducing agents can be used at any suitable concentration, which can be readily determined by one of skill in the art. In general, buffers, cosolvents, salts, detergents/surfactants, chelators, and reducing agents are included in reaction mixtures at concentrations that do not disrupt the lipid assemblies in the liposomes. Buffers, cosolvents, salts, detergents/surfactants, chelators, and reducing agents are typically used in concentrations ranging from about 1 µM to about 100 mM. For example, a buffer, a cosolvent, a salt, a detergent/surfactant, a chelator, or a reducing agent can be included in a reaction mixture at a concentration of about 1 µM, or about 10 µM, or about 100 µM, or about 1 mM, or about 5 mM, or about 10 mM, or about 25 mM, or about 50 mM, or about 100 mM.

Crosslinking of alkyne-functionalized reactive lipids can be conducted via photo-crosslinking reactions, wherein liposomes containing the alkyne-functionalized reactive lipids are exposed to light. In certain embodiments, liposomes containing alkyne-functionalized reactive lipids are exposed to ultraviolet light having a wavelength ranging from about 10 nm to about 380 nm. The wavelength of the ultraviolet light may be, for example, 365 nm or 254 nm. The rate of photo-crosslinking for phospholipids such as 1,2-bis(10,12-tricosadiynoyl)-sn-glycero-3-phosphocholine and 1-palmitoyl-2-(10,12-tricosadiynoyl)-sn-glycero-3-phospho-choline may depend on alignment of alkyne groups in the lipid bilayer of the lipids. As such, efficiency of the photo-crosslinking reactions may be promoted by conducting the reactions at a temperature below the lipid transition temperature (e.g., below 40° C.) so that the hydrocarbon chains are arranged in a crystal-like lattice. For example, photo-crosslinking may be conducted at 25° C., at 4° C., or at 0° C. depending on the particular lipids used for liposome preparation. Any suitable light source, such as a low-pressure mercury arc lamp or a pulsed xenon lamp, can be used for irradiating the liposomes. Irradiation can be conducted for any length of time suitable for obtaining the desired level of crosslinking. Typically, liposomes will be irradiated with ultraviolet light for periods of time ranging from a few seconds to an hour or longer. In some embodiments, irradiation is conducted for less than 45 minutes, or less than 30 minutes, or less than 10 minutes (e.g., 5 minutes, 2 minutes, 1 minute, or 30 seconds). In some embodiments, the photo-crosslinking step is conducted in the presence of a radical initiator such as azobisisobutyronitrile (AIBN); 1-[4-(2-hydroxyethoxy)-phenyl]-2-hydroxy-2-methyl-1-propane-1-one (IRGACURE 2959); 2,2-dimethoxy-1,2-diphenylethan-1-one (IRGACURE 651); and the like. The radical initiator may be included in amounts ranging from about 0.1% (w/w) to about 25% (w/w), or higher, with respect to the total weight of the lipid components. For example, the radical initiator may be used in amounts ranging from about 0.1% (w/w) to about 1% (w/w), or from about 1% (w/w) to about 10% (w/w), or from about 10% (w/w) to about 25% (w/w), or from about 15% (w/w) to 20% (w/w) with respect to the total lipid content.

Typically, the lipid composition will contain the crosslinkers in an amount sufficient to covalently crosslink the lipids in the liposome. The amount of crosslinker present in the lipid composition may be expressed as a mass percentage or a mole percentage of the crosslinkers to the total lipids in the composition. In some embodiments, crosslinkers are present in the lipid composition in an amount ranging from about 1 mol % to about 99 mol %, or from about 10 mol % to about 95 mol %, or from about 15 mol % to about 90 mol %, or from about 20 mol % to about 85 mol %, or from about 25 mol % to about 80 mol %, or from about 30 mol % to about 75 mol %, or from about 35 mol % to about 70 mol %, or from about 40 mol % to about 65 mol %, or from about 45 mol % to about 60 mol %, or from about 50 mol % to about 55 mol %, or from about 1 mol % to about 10 mol %, or from about 10 mol % to about 20 mol %, or from about 20 mol % to about 30 mol %, or from about 30 mol % to about 40 mol %, or from about 40 mol % to about 50 mol %, or from about 50 mol % to about 60 mol %, or from about 60 mol % to about 70 mol %, or from about 70 mol % to about 80 mol %, or from about 80 mol % to about 90 mol %, or from about 90 mol % to about 99 mol % with respect to the total lipid content. In some embodiments, crosslinkers are present in the lipid composition in an amount of at least 10 mol %, at least 20 mol %, at least 30 mol %, at least 40 mol %, at least 50 mol %, at least 60 mol %, at least 70 mol %, at least 80 mol %, at least 90 mol %, at least 95 mol %, or at least 99 mol % with respect to the total lipid content. In some embodiments, 100% of the lipids in the lipid composition are reactive lipids (e.g., 1,2-bis(10,12-tricosadiynoyl)-sn-glycero-3-phosphocholine and the like). In some embodiments, a radical initiator in an amount between 1% and 25% (w/w) with respect to the lipids are used in the crosslinking step. For example, IRGACURE 2959 or IRGACURE 651 can be used in amounts ranging from 10% to 25%, or from 15% to 20% with respect to the total lipid content.

It is not necessary to achieve reaction of each and every crosslinker to covalently crosslink the lipid bilayer, although complete reaction of the crosslinkers is acceptable as well. In some instances, at least 40%, at least 60%, or at least 80% of the crosslinkers are crosslinked. Accordingly, in some embodiments the liposomes contain un-crosslinked reactive lipids. In some embodiments, the un-crosslinked lipids are independently selected from the group consisting of un-crosslinked 2-bis(10,12-tricosadiynoyl)-sn-glycero-3-phosphocholine; un-crosslinked 1-palmitoyl-2-(10,12-tricosadiynoyl)-sn-glycero-3-phospho-choline; un-crosslinked 1,2-bis(10,12-tricosadiynoyl)-sn-glycero-3-phosphoethanolamine; and un-crosslinked 1-palmitoyl-2-(10,12-tricosadiynoyl)-sn-glycero-3-phosphoethanolamine In some embodiments, the method further comprises purifying the liposomes. For example, purifying the liposomes may include removing un-crosslinked liposomes from the bi-directionally crosslinked liposomes. Addition of a surfactant, such as sodium dodecyl sulfate or any of the other non-ionic surfactants, anionic surfactants, or cationic surfactants described above, can be used to break down un-crosslinked vesicles. Detergents in amounts ranging up to about 5% (w/w) may be used for breaking down un-crosslinked vesicles. Crosslinked liposomes can then be recovered using density gradient centrifugation, size exclusion chromatography, filtration, or another suitable technique.

In some embodiments, the methods further include insertion of a targeting agent into the crosslinked liposomes. Suitable targeting agents include, but are not limited to, folic acid derivatives, B-12 derivatives, integrin RGD peptides, NGR derivatives, and somatostatin derivatives or peptides that bind to the somatostatin receptor, e.g., octreotide and octreotate. Targeting agents may include an comprised of DNA, RNA, and/or peptides. The targeting agent can be a targeting lipid having a lipid moiety covalently bonded to a targeting moiety (e.g., a phosphatidylethanolamine-antibody conjugate). The term "insertion" refers to the embedding of a targeting agent into a liposome bilayer. In general, an amphiphilic targeting agent such as a targeting lipid is transferred from solution to a liposome bilayer due to van der Waals interactions between the hydrophobic portion of the amphiphilic lipid and the hydrophobic interior of the bilayer. In some embodiments, insertion of the targeting agent is conducted at a temperature above the gel-to-fluid phase transition temperature ($T_m$) of one or more of the lipid components in the lipid bilayer. The insertion can be conducted, for example, at about 45° C., about 50° C., about 55° C., about 60° C., about 65° C., or at about 70° C. Typically, targeting lipids may be inserted into a lipid membrane in amounts ranging up to about 5% (w/w). Sonication may also be employed during the insertion process. In some embodiments, the method includes insertion of a DSPE-PEG-antibody conjugate into the crosslinked liposomes, wherein the insertion is conducted at 45° C. with sonication.

III. Bi-Directionally Crosslinked Liposomes

In a related aspect, the present invention provides crosslinked liposomes. A population of bi-directionally crosslinked liposomes can be prepared using the methods of the invention. Any of the methods and liposome components (e.g., phospholipids, sterols, crosslinkers, etc.) described above may be used to produce the bi-directionally crosslinked liposomes. The bi-directionally crosslinked liposomes comprise crosslinked lipids arranged in a lipid bilayer having at least two leaflets; the crosslinked lipids may comprise a crosslinked hydrophobic group, a crosslinked hydrophilic group, or a crosslinked hydrophilic group and a crosslinked hydrophobic group; such that the bi-directionally crosslinked liposomes are radially crosslinked and circumferentially crosslinked. The bi-directionally crosslinked liposomes may be useful in the detection or treatment of disease in a subject, particularly in a human subject. In some instances, the population of bi-directionally crosslinked liposomes further comprises a hydrophilic therapeutic agent, a hydrophilic diagnostic agent, or a combination thereof. In some instances, the population of bi-directionally crosslinked liposomes further comprises a hydrophobic therapeutic agent, a hydrophobic diagnostic agent, or a combination thereof.

The lipids in the liposomes may be crosslinked between headgroups or tailgroups or a combination thereof, depending on the particular reactive lipids and crosslinkers used for preparing the liposomes. Tail-to-tail crosslinking or head-to-head crosslinking of adjacent lipids will result in liposomes that are crosslinked circumferentially, whereas tail-to-tail linking across the lipid bilayer will result in liposomes that are crosslinked radially. In multilamellar liposomes, radial crosslinking between headgroups of lipids in adjacent lamellae may also occur.

The liposomes may take the form of unilamellar vesicles, multilamellar vesicles, large unilamellar vesicles or, small unilamellar vesicles. In some embodiments, the liposomes are small unilamellar vesicles. In some embodiments, the liposomes have a largest dimension that is 100 nm or less, 250 nm or less, or 500 nm or less. In some cases, the liposomes have a largest or an average diameter of 100 nm or less, 250 nm or less, or 500 nm or less. In some embodiments, the average size of the population of liposomes is between about 10 µm and about 1 µm in its largest dimension. In some embodiments, the average size is less than about 1 µm in the liposomes' largest dimension. In some embodiments, the average size is between about 1 nm and about 500 nm in the liposomes' largest dimension. In some embodiments, the average size is between about 10 nm and about 200 nm in the liposomes' largest dimension. In some embodiments, the average size is between about 80 nm and 120 nm in the liposomes' largest dimension. In some embodiments, the average size is between about 20 nm and about 120 nm in the liposomes' largest dimension. In some embodiments, the population of liposomes has an average maximum cross-sectional dimension (e.g., diameter) of less than about 1 µm. For example, the average maximum cross-sectional dimension (e.g., diameter) may be between about 5 nm and about 1 µm, between about 10 nm and about 1 µm, less than about 800 nm, less than about 750 nm, less than about 500 nm, less than about 300 nm, less than about 250 nm, less than about 200 nm, less than about 150 nm, or less than about 100 nm. The dimensions of the population of liposomes can be a predetermined dimension, e.g., a cross-sectional diameter, a circumferential dimension, or the like. In some embodiments, the bi-directionally crosslinked liposomes have a polydispersity index (PDI) of 0.20 or less. For example, the PDI may be less than 0.2, less than 0.15, or less than 0.1.

IV. Methods for Delivery of Therapeutic Agents and Diagnostic Agents

Liposomes of the invention can be used for delivery of therapeutic agents, diagnostic agents, and other substances to subjects such as humans or animals. Accordingly, another embodiment of the invention provides a method of delivering a therapeutic agent or diagnostic agent to a subject in need thereof, the method comprising administering liposomes as described above, wherein the liposomes comprise a therapeutic agent or a diagnostic agent. The liposomes may be prepared according to any of the methods described above. In some embodiments, the subject is a human.

The liposomes of the present invention may comprise one or more therapeutic agents present anywhere in, on, or around the liposome. For example, a therapeutic agent may be embedded in the lipid bilayer of the liposome, encapsulated in the aqueous core of the liposome, or tethered to the exterior of the liposome. The therapeutic agent or agents used in the present invention can include any agent directed to treat a condition in a subject. In general, any therapeutic agent known in the art can be used, including without limitation agents listed in the United States Pharmacopeia (U.S.P.), *Goodman and Gilman's The Pharmacological Basis of Therapeutics*, 12th Ed., McGraw Hill, 2011; Katzung, Ed., *Basic and Clinical Pharmacology*, McGraw-Hill/Appleton & Lange, 12th ed., 2012; *Physician's Desk Reference*, 70th Ed., PDR Network, 2016; and/or *The Merck Manual of Diagnosis and Therapy*, 19th ed., Merck Publishing Group, 2011; or, in the case of animals, *The Merck Veterinary Manual*, 10th ed., Merck Publishing Group, 2010; all of which are incorporated herein by reference.

Therapeutic agents can be selected depending on the type of disease desired to be treated. For example, certain types of cancers or tumors, such as carcinoma, sarcoma, leukemia, lymphoma, myeloma, and central nervous system cancers as well as solid tumors and mixed tumors, can involve administration of the same or possibly different therapeutic agents. In certain embodiments, a therapeutic agent can be delivered to treat or affect a cancerous condition in a subject and can include an anticancer agent or cytotoxic agent. Examples of anti-cancer agents include, but are not limited to, alkylating agents (e.g., cyclophosphamide, ifosfamide, melphalan, chlorambucil, aziridines, epoxides, alkyl sulfonates), cisplatin and its analogues (e.g., carboplatin, oxaliplatin), anti m etabolitites (e.g., methotrexate, 5-fluorouracil, capecitabine, cytarabine, gemcitabine, fludarabine), toposiomerase interactive agents (e.g., camptothecin, irinotecan, topotecan, etoposide, teniposide, doxorubicin, daunorubicin), antimicrotubule agents (e.g., *vinca* alkaloids, such as vincristine, vinblastine, and vinorelbine; taxanes, such as paclitaxel and docetaxel), interferons, inteleukin-2, histone deacetylase inhibitors, monoclonal antibodies, estrogen modulators (e.g., tamoxifen, toremifene, raloxifene), megestrol, aromatase inhibitors (e.g., letrozole, anastrozole, exemnestane, octreotide), octreotide, and anti-androgens (e.g., flutamide, casodex).

Corticosteroids may also be included in the liposomes of the invention. Examples of corticosteroids include, but are not limited to, alclometasone, amcinonide, beclomethasone, betamethasone, clobetasol, clocortolone, cortisol, prednisolone, and pharmaceutically acceptable salts, solvates, clathrates, prodrugs, and active metabolites and stereoisomers thereof. Non-steroidal anti-inflammatory drugs (NSAIDs) may also be included in the liposomes of the invention. Examples of NSAIDS include, but are not limited to, acetominaphen, apazone, diclofenac, etodolac, fenoprofen, flurbiprofen, ibuprofen, indomethacin, ketorolac, ketoprofen, meclofenamate, mefenamic acid, meloxicam, nabumetone, naproxen, nimesulide, oxaprozin, oxyphenthatrazone, phenylbutazone, piroxicam, salicylates, sulindac, tenoxicam, and tolmetin. Examples of salicylates include, but are not limited to, aspirin, sodium salicylate, choline magnesium trisalicylate, salsalate, diflunisal, salicylsalicylic acid, sulfasalazine, and olsalazine.

Antihistamines may also be included in the liposomes of the invention. Examples of antihistamines include, but are not limited to, acrivastine, astemizole, brompheniramine, carbinoxamine, cetirazine, chlorcyclizine, chlorpheniramine, clemastine, cyclizine, descarboxyloratadine, dimenhydrinate, diphenhydramine, hydroxyzine, levocabastine, loratadine, promethazine, pyrilamine, terfenadine, and ripelennamine.

Analgesics may also be included in the liposomes of the invention. Examples of analgesics include, but are not limited to, bremazocine, buprenorphine, butorphanol, codeine, diprenorphine, dynorphin A, dynorphin B, β-endorphin, ethylketocyclazocine, etorphine, fentanyl, β-funaltrexamine, heroin, hydrocodone, hydromorphone, leu-enkephalin, levophanol, levallorphan, meptazinol, metenkephalin, methadone, morphine, oxycodone, oxymorphone, nalbuphine, nalmefene, nalorphine, naloxonazine, naloxone, naloxone benzoylhydrazone, naltrexone, naltrindole, α-neoendorphin, nor-binaltorphimine, pentazocine, propoxyphene, and spiradoline.

In addition, the liposomes may also contain immune stimulatory adjuvants, such as aluminum gel or salt adjuvants (e.g., aluminum phosphate or aluminum hydroxide), calcium phosphate, endotoxins, toll-like receptor adjuvants and the like.

Loading of the therapeutic agents can be carried out through a variety of ways known in the art, as disclosed for example in the following references: de Villiers, M. M. et al., Eds., *Nanotechnology in Drug Delivery*, Springer (2009); Gregoriadis, G., Ed., *Liposome Technology: Entrapment of drugs and other materials into liposomes*, CRC Press (2006). Loading of liposomes may be carried out, for example, in an active or passive manner. For example, a therapeutic agent can be included during the self-assembly process of the liposomes. In certain embodiments, the therapeutic agent may also be embedded in the liposome bilayer or within multiple layers of a multilamellar liposome. In alternative embodiments, the therapeutic agent can be actively loaded into liposomes. For example, the liposomes can be exposed to conditions, such as electroporation, in which the bilayer membrane is made permeable to a solution containing therapeutic agent thereby allowing for the therapeutic agent to enter into the internal volume of the liposomes.

The liposomes of the present invention may also contain diagnostic agents. A diagnostic agent used in the present invention may include any diagnostic agent known in the art, as provided, for example, in the following references: *Diagnostic Imaging*, 7$^{th}$ Ed., Wiley-Blackwell, 2013; *Handbook of Targeted Delivery of Imaging Agents*, CRC Press, 1995; and *Molecular Imaging: Radiopharmaceuticals for PET and SPECT*, Springer (2009). A diagnostic agent can be detected by a variety of ways, including as an agent providing and/or enhancing a detectable signal that includes, but is not limited to, gamma-emitting, radioactive, echogenic, optical, fluorescent, absorptive, magnetic or tomography signals. Techniques for imaging the diagnostic agent can include, but are not limited to, single photon emission computed tomography (SPECT), magnetic resonance imaging (MRI), optical imaging, positron emission tomography (PET), computed tomography (CT), x-ray imaging, gamma ray imaging, and the like.

The diagnostic agent may include chelators that bind to metal ions to be used for a variety of diagnostic imaging techniques. Exemplary chelators include but are not limited to ethylenediaminetetraacetic acid (EDTA), [4-(1,4,8,11-tetraazacyclotetradec-1-yl) methyl]benzoic acid (CPTA), cyclohexanediaminetetraacetic acid (CDTA), ethylenebis(oxyethylenenitrilo)tetraacetic acid (EGTA), diethylenetriaminepentaacetic acid (DTPA), citric acid, hydroxyethyl ethylenediamine triacetic acid (HEDTA), iminodiacetic acid (IDA), triethylene tetraamine hexaacetic acid (TTHA), 1,4,7,10-tetraazacyclododecane-1,4,7,10-tetra(methylene phosphonic acid) (DOTP), 1,4,8,11-tetraazacyclododecane-1,4,8,11-tetraacetic acid (TETA), 1,4,7,10-tetraazacyclododecane-1,4,7,10-tetraacetic acid (DOTA), and derivatives thereof.

A radioisotope may be incorporated into the liposomes for diagnostic applications as well as therapeutic applications. Radioisotopes include radionuclides that emit gamma rays, positrons, beta and alpha particles, and X-rays. Suitable radionuclides include but are not limited to $^{225}$Ac, $^{72}$As, $^{211}$At, $^{11}$B, $^{128}$Ba, $^{212}$Bi, $^{75}$Br, $^{77}$Br, $^{14}$C, $^{109}$Cd, $^{62}$Cu, $^{64}$Cu, $^{67}$Cu, $^{18}$F, $^{67}$Ga, $^{68}$Ga, $^{3}$H, $^{123}$I, $^{125}$I, $^{130}$I, $^{131}$I, $^{111}$In $^{177}$Lu, $^{3}$N, $^{15}$O, $^{32}$P, $^{33}$P, $^{212}$Pb, $^{103}$Pd, $^{186}$Re, $^{188}$Re, $^{47}$Sc, $^{153}$Sm, $^{89}$Sr, $^{99m}$Tc, $^{88}$Y and $^{90}$Y. In certain embodiments, radioactive agents can include $^{111}$In-DTPA, $^{99m}$Tc(CO)$_3$-DTPA, $^{99m}$Tc(CO)$_3$-ENPy2, $^{62/64/67}$Cu-TETA, $^{99m}$Tc(CO)$_3$-IDA, and $^{99m}$Tc(CO)$_3$ triamines (cyclic or linear). In other embodiments, the agents can include DOTA and its various analogs with $^{111}$In, $^{177}$Lu, $^{153}$Sm, $^{88/90}$Y, $^{62/64/67}$Cu, or $^{67/68}$Ga. In some embodiments, the liposomes can be radiolabeled, for example, by incorporation of lipids attached to chelates, such as DTPA-lipid, as provided in the following references: Phillips et al., *Wiley Interdisciplinary Reviews: Nanomedicine and Nanobiotechnology*, 1(1): 69-83 (2008); Torchilin, V. P. & Weissig, V., Eds. *Liposomes 2nd Ed.*: Oxford Univ. Press (2003); Elbayoumi, T. A. & Torchilin, V. P., *Eur. J. Nucl. Med. Mol. Imaging* 33:1196-1205 (2006); Mougin-Degraef, M. et al., *Int'l J. Pharmaceutics* 344:110-117 (2007).

In some embodiments, the diagnostic agents may include optical agents such as fluorescent agents, phosphorescent agents, chemiluminescent agents, and the like. Numerous agents (e.g., dyes, probes, labels, or indicators) are known in the art and can be used in the present invention. (See, e.g., Invitrogen, The Handbook—A Guide to Fluorescent Probes and Labeling Technologies, Tenth Edition (2005)). Fluorescent agents can include a variety of organic and/or inorganic small molecules or a variety of fluorescent proteins and derivatives thereof. For example, fluorescent agents can include but are not limited to cyanines, phthalocyanines, porphyrins, indocyanines, rhodamines, phenoxazines, phenylxanthenes, phenothiazines, phenoselenazines, fluoresceins, benzoporphyrins, squaraines, dipyrrolo pyrimidones, tetracenes, quinolines, pyrazines, corrins, croconiums, acridones, phenanthridines, rhodamines, acridines, anthraquinones, chalcogenopyrylium analogues, chlorins, naphthalocyanines, methine dyes, indolenium dyes, azo compounds, azulenes, azaazulenes, triphenyl methane dyes, indoles, benzoindoles, indocarbocyanines, benzoindocarbocyanines, and BODIPY™ derivatives having the general structure of 4,4-difluoro-4-bora-3a,4a-diaza-s-indacene, and/or conjugates and/or derivatives of any of these.

One of skill in the art will appreciate that particular optical agents used can depend on the wavelength used for excitation, depth underneath skin tissue, and other factors generally well known in the art. For example, optimal absorption or excitation maxima for the optical agents can vary depending on the agent employed, but in general, the optical agents of the present invention will absorb or be excited by light in the ultraviolet (UV), visible, or infrared (IR) range of the electromagnetic spectrum. For imaging, dyes that absorb and emit in the near-IR (~700-900 nm, e.g., indocyanines) are preferred. For topical visualization using an endoscopic method, any dyes absorbing in the visible range are suitable.

In some embodiments, the diagnostic agents can include but are not limited to magnetic resonance (MR) and x-ray contrast agents that are generally well known in the art, including, for example, iodine-based x-ray contrast agents, superparamagnetic iron oxide (SPIO), complexes of gadolinium or manganese, and the like. (See, e.g., Armstrong et al., *Diagnostic Imaging*, 5$^{th}$ Ed., Blackwell Publishing (2004)). In some embodiments, a diagnostic agent can include a magnetic resonance (MR) imaging agent. Exemplary magnetic resonance agents include but are not limited to paramagnetic agents, superparamagnetic agents, and the like. Exemplary paramagnetic agents can include but are not limited to gadopentetic acid, gadoteric acid, gadodiamide, gadolinium, gadoteridol, mangafodipir, gadoversetamide, ferric ammonium citrate, gadobenic acid, gadobutrol, or gadoxetic acid. Superparamagnetic agents can include but are not limited to superparamagnetic iron oxide and ferristene. In certain embodiments, the diagnostic agents can include x-ray contrast agents. Examples of x-ray contrast agents include, without limitation, iopamidol, iomeprol, iohexol, iopentol, iopromide, iosimide, ioversol, iotrolan, iotasul, iodixanol, iodecimol, ioglucamide, ioglunide, iogulamide, iosarcol, ioxilan, iopamiron, metrizamide, iobitridol and iosimenol. In certain embodiments, the x-ray contrast agents can include iopamidol, iomeprol, iopromide, iohexol, iopentol, ioversol, iobitridol, iodixanol, iotrolan and iosimenol.

As for the therapeutic agents described above, the diagnostic agents can be associated with the liposome in a variety of ways, including for example being embedded or encapsulated in the liposome. Similarly, loading of the diagnostic agents can be carried out through a variety of ways known in the art, as disclosed for example in the following references: de Villiers, M. M. et al., Eds., *Nanotechnology in Drug Delivery*, Springer (2009); Gregoriadis, G., Ed., *Liposome Technology: Entrapment of drugs and other materials into liposomes*, CRC Press (2006).

In some cases, liposome accumulation at a target site may be due to the enhanced permeability and retention characteristics of certain tissues such as cancer tissues. Accumulation in such a manner often results in part because of liposome size and may not require special targeting functionality. In other cases, delivery of therapeutic agents and/or diagnostic agents may be targeted to a location in the subject. Accordingly, some embodiments of the invention provide delivery methods wherein the liposomes further include a targeting agent. Generally, the targeting agents of the present invention can associate with any target of interest, such as a target associated with an organ, tissues, cell, extracellular matrix, or intracellular region. In some embodiments, a target can be associated with a particular disease state, such as a cancerous condition. In some embodiments, the targeting component can be specific to only one target, such as a receptor. Suitable targets can include but are not limited to a nucleic acid, such as a DNA, RNA, or modified derivatives thereof. Suitable targets can also include but are not limited to a protein, such as an extracellular protein, a receptor, a cell surface receptor, a tumor-marker, a transmembrane protein, an enzyme, or an antibody. Suitable targets can include a carbohydrate, such as a monosaccharide, disaccharide, or polysaccharide that can be, for example, present on the surface of a cell.

In some embodiments, the targeting agent may include a target ligand (e.g., an RGD-containing peptide), a small molecule mimic of a target ligand (e.g., a peptide mimetic ligand), or an antibody or antibody fragment specific for a particular target. In some embodiments, a targeting agent may include folic acid derivatives, B-12 derivatives, integrin RGD peptides, NGR derivatives, somatostatin derivatives or peptides that bind to the somatostatin receptor, e.g., octreotide and octreotate, and the like. In some embodiments, the targeting agents of the present invention may include an aptamer. Aptamers can be designed to associate with or bind to a target of interest. Aptamers can be comprised of, for example, DNA, RNA, and/or peptides, and certain aspects of aptamers are well known in the art. (See. e.g., Klussman, S., Ed., The Aptamer Handbook, Wiley-VCH (2006); Nissenbaum, E. T., *Trends in Biotech.* 26(8): 442-449 (2008)).

Liposomes of the invention are typically administered in conjunction with a physiologically (i.e., pharmaceutically) acceptable carrier. As used herein, the term "carrier" refers to a typically inert substance used as a diluent or vehicle for a drug such as a therapeutic agent. Typically, the physiologically acceptable carriers are present in liquid form. Examples of liquid carriers include physiological saline, phosphate buffer, normal buffered saline (135-150 mM NaCl), water, buffered water, 0.4% saline, 0.3% glycine, glycoproteins to provide enhanced stability (e.g., albumin, lipoprotein, globulin, etc.), and the like. Since physiologically acceptable carriers are determined in part by the particular composition being administered as well as by the particular method used to administer the composition, there are a wide variety of suitable formulations of pharmaceutical compositions of the present invention (See, e.g., *Remington: The Science and Practice of Pharmacy*, $21^{st}$ ed., 2005).

Compositions containing liposomes of the present invention may be sterilized by conventional, well-known sterilization techniques or may be produced under sterile conditions. Aqueous solutions can be packaged for use or filtered under aseptic conditions and lyophilized, the lyophilized preparation being combined with a sterile aqueous solution prior to administration. Compositions containing liposomes may contain pharmaceutically acceptable auxiliary substances as required to approximate physiological conditions, such as pH adjusting and buffering agents, tonicity adjusting agents, wetting agents, and the like, e.g., sodium acetate, sodium lactate, sodium chloride, potassium chloride, calcium chloride, sorbitan monolaurate, and triethanolamine oleate. Sugars can also be included for stabilizing the compositions, such as a stabilizer for lyophilized liposome compositions.

Formulations suitable for parenteral administration, such as, for example, by intravenous, intramuscular, intratumoral, intradermal, intraperitoneal, intraarticular (in the joints), and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Injection solutions and suspensions can also be prepared from sterile powders, granules, and tablets. In the practice of the present invention, compositions can be administered, for example, by intravenous infusion, topically, intraperitoneally, intravesically, or intrathecally. Parenteral administration and intravenous administration are the preferred methods of administration. The formulations of liposome compositions can be presented in unit-dose or multi-dose sealed containers, such as ampoules and vials.

Liposomes containing a therapeutic and/or diagnostic agent may be administered at the initial dosage of about 0.001 mg/kg to about 1000 mg/kg daily. For example, a daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg may be used. The dosages, however, may be varied depending upon the requirements of the subject, the severity of the condition being treated, the nature of the therapeutic agent, and the liposome composition being employed. For example, dosages can be empirically determined considering the type and stage of cancer diagnosed in a particular subject. The dose administered to a subject, in the context of the present invention, should be sufficient to affect a beneficial therapeutic response in the subject over time. The size of the dose will also be determined by the existence, nature, and extent of any adverse side-effects that accompany the administration of a particular liposome composition in a particular subject. Determination of the proper dosage for a particular situation is within the skill of the practitioner. Generally, treatment is initiated with smaller dosages which are less than the optimum dose of the liposome composition. Thereafter, the dosage is increased by small increments until the optimum effect under circumstances is reached. For convenience, the total daily dosage may be divided and administered in portions during the day, if desired. In certain embodiments, the rate of release of an active agent or a diagnostic agent from the crosslinked liposomes may be controlled by the level of crosslinking in the liposomes.

V. Example 20-mL scintillation vials are stored in oven at 230° C. for at least 2 hours prior to lipid film preparation. DPPE (12+/−0.3 mg) is weighed in a 20-mL scintillation vial, and cholesterol (4 mg) is added as a 10 mg/mL stock solution chloroform:methanol (2:1 v/v). 1,2-bis(10,12-tricosadiynoyl)-sn-glycero-3-phosphoethanolamine [DC(8,9)PE] is added in an amount equal to 5 mol % with respect to the total lipid mixture. 1-(20,22-tricosadiynoyl)-2-(10,12-tricosadiynoyl)-sn-glycero-3-phosphoethanolamine is further added in an amount equal to 5 mol % with respect to the total lipid mixture. In some cases, DPPE-Cy5.5 (0.4 mg) is added as a 1 mg/mL stock solution in chloroform:methanol (2:1 v/v). In some cases, DSPE-PEG5K is added in an amount equal to 5 mol % with respect to the total lipid mixture.

5 mL of chloroform:methanol (2:1 v/v) is added to the 20-mL scintillation vial and the lipid components are completely dissolved. The solvents are removed using a rotary evaporator to form a uniform lipid film around the bottom of the 20-mL scintillation vial. The vial is sealed with perforated parafilm and placed in a dessicator for at least 2 hours to remove all volatile organics.

5 mL of hydration buffer (freshly prepared 10 mM HEPES, pH=7.4) is added to the 20-mL scintillation vial and sonicated. The mixture is cooled to room temperature and then diluted with PBS to 3 times the total volume. The resulting liposomes are concentrated to approximately 3-4 mL total volume via spin filtration in 30 kDa MWCO filters. The liposomes are combined with IRGACURE 651 (2,2-dimethoxy-1,2-diphenylethan-1-one; 1 mol % or 10 mol %), and UV-crosslinking by irradiation at 365 nm is conducted for between 1 and 10 minutes. Covalent bonds are formed between adjacent lipids in each of the two leaflets of the lipid bilayer, as well as across leaflets in the lipid bilayer.

Although the foregoing has been described in some detail by way of illustration and example for purposes of clarity and understanding, one of skill in the art will appreciate that certain changes and modifications can be practiced within the scope of the appended claims. In addition, each reference provided herein is incorporated by reference in its entirety to the same extent as if each reference was individually incorporated by reference.

What is claimed is:

1. A method of producing bi-directionally crosslinked unilamellar liposomes, comprising the steps of:
   providing a lipid composition comprising a plurality of reactive lipids, wherein each of the reactive lipids comprises a reactive hydrophobic group, a reactive hydrophilic group, or a reactive hydrophilic group and a reactive hydrophobic group;
   forming an un-crosslinked liposome comprising the reactive lipids; and
   crosslinking at least a portion of the reactive hydrophobic groups, at least a portion of the reactive hydrophilic groups, or at least a portion of the reactive hydrophobic groups and at least a portion of the hydrophilic groups;
   thereby producing the bi-directionally crosslinked liposomes,
   wherein the bi-directionally crosslinked liposomes are radially crosslinked and circumferentially crosslinked,
   wherein the radial crosslinks comprise covalent bonds between two layers of the lipid bilayer, and
   wherein the circumferential crosslinks comprise covalent bonds between lipids in the same layer of the lipid bilayer.

2. The method of claim 1, wherein the reactive lipids in the un-crosslinked liposome are arranged in a lipid bilayer having at least two leaflets and wherein:
   crosslinking the reactive hydrophobic groups comprises forming covalent bonds between the reactive hydrophobic groups of adjacent reactive lipids within the same leaflet;
   crosslinking the reactive hydrophobic groups comprises forming covalent bonds between the reactive hydrophobic groups of adjacent reactive lipids across different leaflets; or
   crosslinking the reactive hydrophobic groups comprises forming covalent bonds between the reactive hydrophobic groups of adjacent reactive lipids within the same leaflet and between the reactive hydrophobic groups of adjacent reactive lipids across different leaflets.

3. The method of claim 1, wherein:
   the reactive hydrophobic groups comprise one or more carbon-carbon double bonds, one or more carbon-carbon triple bonds, one or more azide groups, one or more thiol groups, or a combination thereof;
   the reactive hydrophilic groups comprise one or more carbon-carbon double bonds, one or more carbon-carbon triple bonds, one or more azide groups, one or more thiol groups, or a combination thereof; or
   the reactive hydrophobic groups and the reactive hydrophilic groups comprise one or more carbon-carbon double bonds, one or more carbon-carbon triple bonds, one or more azide groups, one or more thiol groups, or a combination thereof.

4. The method of claim 1, wherein each reactive lipid is independently selected from the group consisting of 1,2-bis(10,12-tricosadiynoyl)-sn-glycero-3-phosphocholine; 1-palmitoyl-2-(10,12-tricosadiynoyl)-sn-glycero-3-phosphocholine; 1,2-bis(10,12-tricosadiynoyl)-sn-glycero-3-phosphoethanolamine; and 1-palmitoyl-2-(10,12-tricosadiynoyl)-sn-glycero-3-phosphoethanolamine.

5. The method of claim 1, wherein:
   crosslinking the reactive hydrophobic groups of the component lipids comprises contacting the reactive hydrophobic groups with a non-lipid crosslinking reagent;
   crosslinking the reactive hydrophilic groups of the component lipids comprises contacting the reactive hydrophilic groups with a non-lipid crosslinking reagent; or
   crosslinking the reactive hydrophobic groups of the component lipids comprises contacting the reactive hydrophobic groups with a non-lipid crosslinking reagent and crosslinking the reactive hydrophilic groups of the component lipids comprises contacting the reactive hydrophilic groups with a non-lipid crosslinking reagent.

6. The method of claim 5, wherein the non-lipid crosslinking reagent comprises one or more carbon-carbon double bonds, one or more carbon-carbon triple bonds, one or more azide groups, or a combination thereof.

7. The method of claim 5, wherein the crosslinking reagent is selected from the group consisting of an amine-reactive homobifunctional crosslinker, a thiol-reactive homobifunctional crosslinker, an amine- and thiol-reactive heterobifunctional crosslinker, and combinations thereof.

8. The method of claim 1, wherein the lipid composition and the liposomes further comprise a plurality of non-reactive lipids.

9. The method of claim 8, wherein each of the non-reactive lipids is independently selected from the group consisting of a phosphatidylcholine, a PEGylated phosphatidylethanolamine, and a sterol.

10. The method of claim 8, wherein the lipid composition and the liposomes are substantially free of cholesterol or cholesterol derivatives.

11. The method of claim 1, wherein:
the bi-directionally crosslinked liposomes have an average diameter of 100 nanometers or less;
the bi-directionally crosslinked liposomes have a polydispersity index of 0.20 or less; or
the bi-directionally crosslinked liposomes have an average diameter of 100 nanometers or less and a polydispersity index of 0.20 or less.

12. A population of bi-directionally crosslinked unilamellar liposomes produced by the method of claim 1, wherein the bi-directionally crosslinked unilamellar liposomes are radially crosslinked and circumferentially crosslinked, wherein the radial crosslinks comprise covalent bonds between two layers of the lipid bilayer, and wherein the circumferential crosslinks comprise covalent bonds between lipids in the same layer of the lipid bilayer.

13. The population of bi-directionally crosslinked liposomes according to claim 12, further comprising a therapeutic agent, diagnostic agent, or a combination thereof.

14. A population of bi-directionally crosslinked unilamellar liposomes comprising crosslinked lipids arranged in a lipid bilayer having two leaflets,
wherein the crosslinked lipids comprise a crosslinked hydrophobic group, a crosslinked hydrophilic group, or a crosslinked hydrophilic group and a crosslinked hydrophobic group,
wherein the bi-directionally crosslinked liposomes are radially crosslinked and circumferentially crosslinked,
wherein the radial crosslinks comprise covalent bonds between two layers of the lipid bilayer, and
wherein the circumferential crosslinks comprise covalent bonds between lipids in the same layer of the lipid bilayer.

15. The population of bi-directionally crosslinked liposomes according to claim 14, wherein each of the crosslinked lipids is independently selected from the group consisting of crosslinked 2-bis(10,12-tricosadiynoyl)-sn-glycero-3-phosphocholine; crosslinked 1-palmitoyl-2-(10,12-tricosadiynoyl)-sn-glycero-3-phosphocholine; crosslinked 1,2-bis(10,12-tricosadiynoyl)-sn-glycero-3-phosphoethanolamine; and crosslinked 1-palmitoyl-2-(10,12-tricosadiynoyl)-sn-glycero-3-phosphoethanolamine.

16. The population of bi-directionally crosslinked liposomes according to claim 14, further comprising a plurality of un-crosslinked lipids.

17. The population of bi-directionally crosslinked liposomes according to claim 16, wherein each of the un-crosslinked lipids is independently selected from the group consisting of a phosphatidylcholine and a PEGylated phosphatidylethanolamine.

18. The population of bi-directionally crosslinked liposomes according to claim 17, which are substantially free of cholesterol or cholesterol derivatives.

19. The population of bi-directionally crosslinked liposomes according to claim 14, wherein:
the bi-directionally crosslinked liposomes have an average diameter of 100 nanometers or less;
the bi-directionally crosslinked liposomes have a polydispersity index of 0.20 or less; or
the bi-directionally crosslinked liposomes have an average diameter of 100 nanometers or less and a polydispersity index of 0.20 or less.

20. The population of bi-directionally crosslinked liposomes according to claim 14, further comprising a therapeutic agent, diagnostic agent, or a combination thereof.

* * * * *